United States Patent

Bloch

[11] 4,050,292
[45] Sept. 27, 1977

[54] METHOD AND APPARATUS FOR TESTING RAILROAD WHEELS

[75] Inventor: Peter K. Bloch, Old Greenwich, Conn.

[73] Assignee: Krautkramer-Branson, Incorporated, Stratford, Conn.

[21] Appl. No.: 733,444

[22] Filed: Oct. 18, 1976

[51] Int. Cl.² ............................................. G01N 29/04
[52] U.S. Cl. ............................... 73/67.5 R; 73/67.8 S
[58] Field of Search ............... 73/67.5 R, 67.7, 67.8 R, 73/67.8 S, 67.9, 71.5 US

[56] References Cited

U.S. PATENT DOCUMENTS

| 3,266,300 | 8/1966 | Graboski | 73/71.5 US |
| 3,349,609 | 10/1967 | Ryzhov-Nikonov et al. | 73/67.9 |
| 3,367,173 | 2/1968 | Uphoff | 73/67.8 R |
| 3,596,503 | 8/1971 | Gay et al. | 73/67.8 S |
| 3,978,712 | 9/1976 | Cowan et al. | 73/67.5 R |

Primary Examiner—Richard C. Queisser
Assistant Examiner—Stephen A. Kreitman
Attorney, Agent, or Firm—Ervin B. Steinberg; Philip J. Feig

[57] ABSTRACT

An ultrasonic pulse-echo apparatus tests railroad wheels passing through a test zone by sending ultrasonic energy into the rim of the wheels. Sensing means are disposed to discern the type of wheel e.g. locomotive wheel or freight car wheel to be tested and provide a corresponding control signal which adjusts the sensitivity of the test apparatus. This arrangement causes the apparatus to be conditioned for registering relatively small defects in locomotive wheels, but passing over small defects in other wheels which are stressed to a lesser extent, e.g. freight car wheels. Hence, the sensitivity of the test apparatus is continuously responsive to the wheel category undergoing test.

9 Claims, 1 Drawing Figure

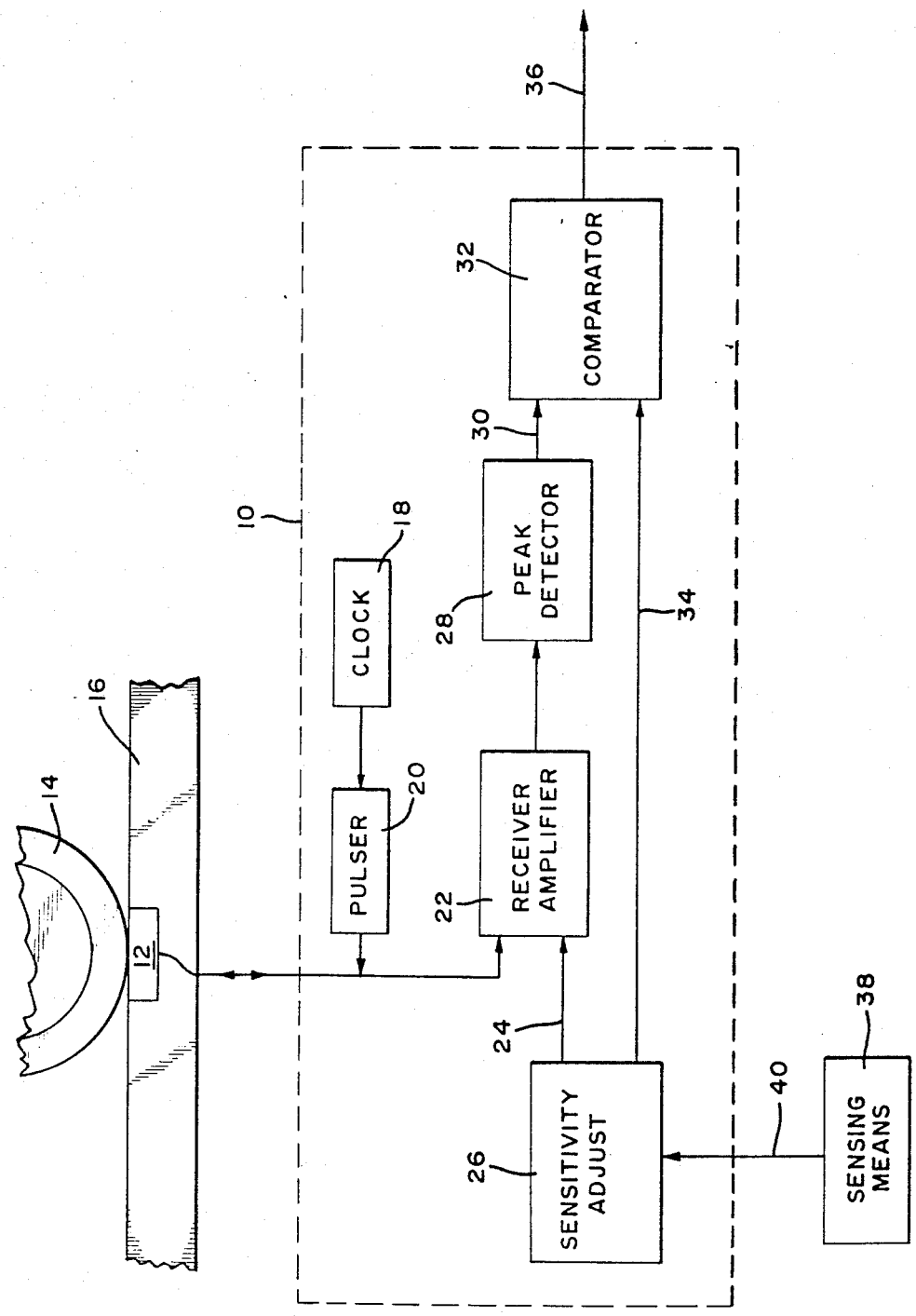

METHOD AND APPARATUS FOR TESTING RAILROAD WHEELS

BRIEF SUMMARY OF THE INVENTION

The present invention refers to a method and apparatus for testing railroad wheels using ultrasonic energy. More specifically, the instant invention concerns an apparatus for detecting defects of differing minimum magnitudes in different categories of wheels depending upon the stress to which the wheels are subjected.

It is well known that wheel failures caused for instance by wear or thermal cracks are a major source of train derailment. It is also known that certain wheels experience greater stress than others. For instance, locomotive wheels due to the weight of the locomotive and tractive effort experience greater stress than wheels of other cars. As a result, defects of a relatively minor magnitude in a locomotive wheel create a greater likelihood of failure than a comparatively larger defect in the wheel of another car in the train. Therefore, it is desireable to provide a method and apparatus for testing wheels using an apparatus readily capable of being conditioned for having a different sensitivity for a first category of wheels which experience greater stress than for testing a second category of wheels which experience a smaller stress.

Testing of railroad wheels using ultrasonic energy is known. For instance, in U.S. Pat. No. 3,812,708, dated May 28, 1974, to J. V. Cowan et al., entitled "Method and Apparatus For Testing Wheels and Defect Detection in Wheels" a method and apparatus for testing railroad wheels in a test zone using ultrasonic energy is disclosed.

In a typical wheel defect detection arrangement of the type described in the stated patent an ultrasonic energy search signal from an electroacoustic transducer probe is transmitted into the rim of a wheel. Upon intercepting a defect or flaw, a portion of the search signal is reflected back toward the transducer probe as a defect responsive echo signal. The echo signal is provided from the transducer probe to an amplifier circuit which, in turn, conducts the amplified echo responsive signal to a peak detector circuit. The peak detector circuit generates an electrical signal indicative of the peak value of the amplified defect responsive echo signal. The peak value signal is provided further to a comparator circuit for providing a defect responsive signal in the event the peak value signal exceeds a predetermined direct current voltage level signal. The amplitude of the voltage level signal is commensurate with the minimum detectable defect magnitude of a defect or flaw manifest in the wheel.

The defect responsive echo signal amplitude is commensurate with the magnitude of a flaw or defect in the wheel. The minimum magnitude of a defect manifest in the wheel to be detected is varied by suitable adjustment of the amplifier circuit gain, the amplifier circuit attenuation or the predetermined voltage level signal to the comparator circuit, in any combination.

In the present invention, the defect detection unit includes means for being selectively adjusted to detect small magnitude defects in a wheel subjected to large stress (e.g. locomotive wheels), and to detect only larger magnitude defects in a wheel experiencing lower stress.

The apparatus, in accordance with this invention, includes sensing means for determining the category of wheels entering the test zone and for adjusting responsive to such determination the minimum detectable defect magnitude. Since a train may have more than one locomotive, locomotives in both the front and/or rear of the train, or the train can enter the test zone traveling in either a forward or backward direction, an automatic sensing means capable of distinguishing one category of wheels, such as locomotive wheels, from another category of wheels is necessary. Such sensing means can include a strain gage embedded in the rail in proximity to the test zone to signal the approach of a heavy locomotive. Alternatively, an optical scanner can be disposed for reading coded information on the side of a freight car for providing a signal indicating the approach of a freight car. Moreover, a manual switch can be triggered when a locomotive approaches the test zone for providing a signal to adjust the detect detection unit as will be explained below. Other sensing means including pattern recognition means can be used to distinguish between categories of wheels or vehicles.

This invention, therefore, embodies a practical method and apparatus for rapidly testing all the wheels of a train while rejecting only those wheels which manifest defects considered sufficiently large to present a danger of a derailment.

A principal object of this invention, therefore, is the provision of an automatic wheel tester for detecting defects of different magnitudes in different categories of wheels.

Another object of this invention is the provision of an arrangement of detecting smaller defects in a category of wheels which are subject to larger stress.

A further object of the invention is the provision of sensing means associated with a wheel testing circuit for changing the sensitivity of a defect detection unit responsive to the category of wheels sensed by such sensing means.

Further and still other objects of the invention will become more readily apparent when the specification is read in conjunction with the accompanying drawing.

BRIEF DESCRIPTION OF THE DRAWINGS

The sole FIGURE is an electrical schematic block diagram of a preferred embodiment of the invention.

DETAILED DESCRIPTION OF THE INVENTION

Referring to the FIGURE, a defect detection unit 10 and an associated transducer probe 12 are shown for testing a wheel 14 traveling along rail 16. The probe 12 while illustrated as a single transmit-receiver transducer probe may comprise an array of probes embedded in the rail 16 for forming a test zone as shown for instance in Cowan et al supra.

The defect detection unit 10 includes a clock 18 for cyclically providing when actuated a transmit signal to a pulser 20 at a predetermined frequency, typically at a frequency between 500 hertz and 10 kilohertz. The pulser 20 upon receipt of a clock signal provides a high voltage transmit pulse to probe 12 for causing the transducer probe 12 to transmit an acoustic energy search signal into the rim of the wheel 14. The search signal typically is in the frequency range between 0.5 and 10 megahertz. A portion of the search signal upon intercepting a defect or flaw in the wheel 14 is reflected back toward the probe 12.

The amplitude of the defect responsive echo signal is indicative of the magnitude of the intercepted defect or flaw in the wheel 14. By adjusting the sensitivity of the defect detection unit for detecting defect responsive echo signals which exceed a predetermined minimum amplitude, only wheel defects of a magnitude exceeding a predetermined minimum magnitude will cause a defect present signal to be manifest at the output of the defect detection unit.

The defect responsive echo signal received by the probe 12 is conducted to one input of a receiver amplifier circuit 22 where the defect responsive echo signal is amplified. The other input of receiver amplifier circuit 22 is connected via conductor 24 to a sensitivity adjust circuit 26. The gain of the receiver amplifier 22 varies in relation to the amplitude of the signal from the sensitivity circuit 26 along conductor 24 to the amplifier 22. By adjusting the amplitude of the signal along conductor 24 responsive to the category of wheels 14 under test, the gain of the receiver amplifier 22 is varied and, hence, the sensitivity of the defect detection unit 10 is varied.

It is also known that the receiver amplifier circuit 22 may include serially connected attenuator circuits. It will be apparent that in an alternative embodiment of amplifier circuit 22, a signal along conductor 24 can be used to vary the signal attenuation in amplifier circuit 22 and thereby also vary the sensitivity of the defect detection unit 10.

The output of amplifier circuit 22 is conducted to a peak detector circuit 28 for providing at the output of the latter circuit a direct current signal commensurate with the peak value of the amplified defect responsive echo signal.

The peak value of the amplified defect responsive echo signal is conducted from peak detector 28 via conductor 30 to one input of a comparator circuit 32. The other input of comparator circuit 32 is connected via conductor 34 to sensitivity adjust circuit 26. The comparator circuit 32 compares the amplitude of the peak value signal along conductor 30 with the amplitude of the direct current voltage level signal provided along conductor 34. The amplitude of the voltage level signal is commensurate with the minimum defect magnitude detectable. An output signal from the comparator circuit 32 indicates the presence of a defect in the wheel under test exceeding a predetermined magnitude. The defect present signal along conductor 36 is provided to a device for marking the defective wheel or to any other suitable defect recording means.

Sensing means 38 is disposed for detecting the approach of a wheel into the test zone and classifying the wheel into a predetermined category. The sensing means, in a preferred embodiment, comrises a strain gage embedded in the rail in proximity to the test zone. When a locomotive, usually a heavier vehicle than other cars in a train, passes over the strain gage a first signal is provided along conductor 40 to the sensitivity adjust circuit 26. When a car other than a locomotive passes over the strain gage, a second signal is provided along conductor 40. Hence, the amplifier 22 is conditioned responsive to the categories of wheels. Similarly, comparator 32 via the signal along conductor 34 is conditioned responsive to the categories of wheels.

Alternatively, a sensing device for reading color bar codes on the side of a freight car may be used to distinguish such car from a locomotive. Moreover, a switch can be used as a sensing means when the switch is disposed for being triggered by one category of rail car and not another. The specific sensing means 40 used to distinguish different categories of wheels is not critical to the present invention and any other suitable means can be employed.

In operation, the signal along conductor 40 is received by the sensitivity adjust circuit 26. In a typical example where the cars are classified as either locomotive or not locomotive, sensitivity adjust circuit 26 may comprise a relay switch. The relay switch contacts a first set of contacts when a locomotive wheel enters the test zone and contacts a second set of contacts when the wheel of another car enters the zone. When a locomotive wheel 14 is tested, the gain of amplifier circuit 22 is increased or the attenuation of the amplifier circuit 22 is decreased, or the direct current voltage signal amplitude along conductor 34 is decreased for maximizing the sensitivity of the defect detection unit 10. In this manner, small defects manifest in the locomotive wheel 14 cause a defect present signal to be apparent along conductor 36. Conversely, when another car wheel 14 is tested, the relay in sensitivity adjust circuit 26 changes contacts and lowers the gain (or increases the attenuation) of amplifier circuit 22 or increases the direct current voltage level signal along conductor 34 to comparator circuit 32. Under such circumstances, the defect detection unit 10 will not detect defects of a smaller magnitude than a predetermined size. Hence, when a railroad wheel other than a locomotive wheel is tested, only large defects manifest in the wheel will cause a defect present signal to be manifest along conductor 36.

While in the above description, either the gain or the attenuation of the receiver amplifier circuit 22 or the direct current voltage level signal to comparator 32 is adjusted, it will be apparent to those skilled in the art that more than one adjustment may be made in practicing the invention. Moreover, it is possible when selecting a plurality of wheel categories that the gain of circuit 22 and the signal provided along conductor 32 may be varied incrementally or continuously and not in the step manner described above. Moreover, other parameters of the defect detection unit 10 can be varied for changing the sensitivity of the unit 10 responsive to being conditioned by the sensing means 40 of the approach of wheels of different categories entering the test zone.

As stated heretofore, optical sensing means can be used also for developing a signal indicative of freight cars, locomotives or other cars. Instead of optical sensing means, electromagnetic radiation means may be used in a similar manner for producing a signature peculiar to a certain category of vehicles and, hence, of the wheel type.

While there has been described and illustrated a preferred embodiment of a wheel tester and several modifications have been indicated, it will be apparent to those skilled in the art that further modifications and variations may be made therein without deviating from the broad principle of the invention which shall be limited solely by the scope of the appended claims.

What is claimed is:

1. A method for testing railroad wheels in a test zone comprising the steps of:
    sensing the presence in the test zone of a wheel falling within a first category or a wheel falling within a second category and providing a corresponding control signal;
    transmitting an acoustic energy search signal into the wheel and receiving defect responsive echo signals therefrom;

selectively detecting responsive to said control signal defects of a first magnitude in a wheel falling within said first category and defects of a second magnitude in a wheel falling within said second category.

2. A method for testing as set forth in claim 1, said selectively detecting comprising changing the detection level for different defect magnitudes.

3. An apparatus for testing railroad wheels in a test zone comprising:
sensing means disposed for detecting the presence of a wheel falling within a first category or a wheel falling within a second category and providing a corresponding control signal;
ultrasonic defect detection means disposed in the test zone and adapted to be conditioned to selectively detect defects in the wheel of a first magnitude and of a second magnitude, and
means coupling said control signal to said defect detection means for conditioning said detection means responsive to said control signal.

4. An apparatus as set forth in claim 3, said sensing means being responsive to the weight on the wheel to be tested.

5. An apparatus as set forth in claim 3, said sensing means being responsive to the type of vehicle to which a wheel is coupled.

6. An apparatus as set forth in claim 3, said control signal changing the gain of said defect detection means.

7. An apparatus as set forth in claim 3, said control signal adjusting signal attenuation means forming a part of said detection means.

8. An apparatus as set forth in claim 3, said control signal changing the detection level of said detection means.

9. An apparatus for testing railroad wheels comprising:
sensing means disposed for detecting the presence of a wheel falling within different categories and providing a category responsive control signal;
ultrasonic defect detection means disposed for detecting defects in a wheel; and
means coupling said category responsive control signal to said defect detection means for conditioning the sensitivity of said detection means responsive to said control signal.

* * * * *